US00PP30235P2

(12) United States Plant Patent
Krebs

(10) Patent No.: US PP30,235 P2
(45) Date of Patent: Feb. 26, 2019

(54) ***RHODODENDRON* PLANT NAMED 'HOLDEN52'**

(50) Latin Name: *Rhododendron hybrida*
Varietal Denomination: HOLDEN52

(71) Applicant: Stephen Krebs, Kirtland, OH (US)

(72) Inventor: Stephen Krebs, Kirtland, OH (US)

(73) Assignee: Plant Development Services, Inc, Loxley, AL (US)

( * ) Notice: Subject to any disclaimer, the term of this patent is extended or adjusted under 35 U.S.C. 154(b) by 0 days.

(21) Appl. No.: 15/732,123

(22) Filed: Sep. 19, 2017

(51) Int. Cl.
*A01H 5/00* (2018.01)

(52) U.S. Cl.
USPC ..... Plt./239

(58) Field of Classification Search
USPC ..... Plt./226, 238, 239
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Rhododendron* cultivar named 'HOLDEN52' is disclosed, characterized by colorful rose-pink flowers with definite white and light pink patterning. Plants are heat tolerant to USDA zone 9 and cold hardy to Zone 5. Resistance to *Phytophthora* root rot has been observed. Plants have a dense, mounded habit and dark green, glossy mature foliage. The new cultivar is a *Rhododendron*, suitable for ornamental garden purposes.

2 Drawing Sheets

Figure 1:
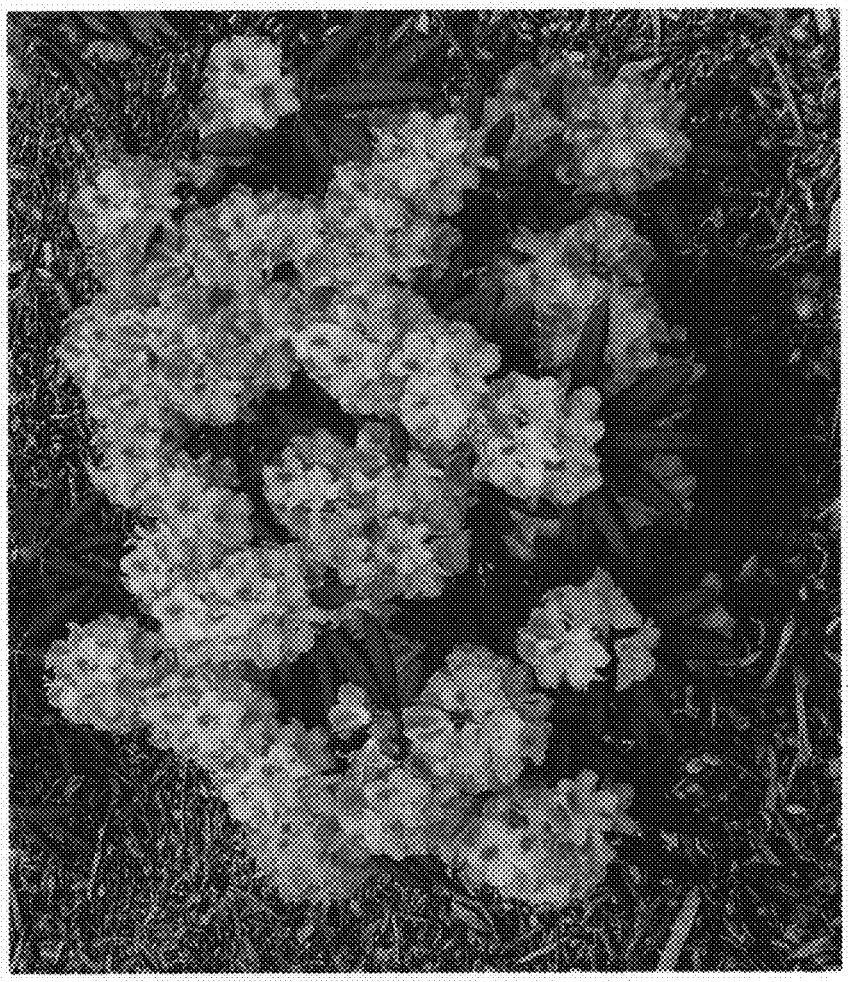

Latin name of the genus and species: *Rhododendron hybrida.*

Variety denomination: 'HOLDEN52'.

BACKGROUND OF THE INVENTION

The new cultivar is a product of a planned breeding program. This new variety, hereinafter referred to as 'HOLDEN52', was discovered as a seedling, resulting from the crossing of an unpatented, unnamed *Rhododendron hyperthyrum* with the pollen parent *Rhododendron hybrida* 'Henry's Red', unpatented. The cross resulting in the new variety occurred during 2005. The new variety was selected by the inventor during of 2010 at an arboretum in Madison, Ohio.

After identifying the new variety as a potentially interesting selection, the inventor first organized propagation of 'HOLDEN52' by vegetative cuttings Fall of 2007 at the same arboretum in Madison, Ohio. The inventor continued controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'HOLDEN52' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'HOLDEN52' These characteristics in combination distinguish 'HOLDEN52' as a new and distinct *Rhododendron* cultivar:

1. Colorful rose-pink flowers with definite white and light pink patterning and dark red speckles located on the central upper petal.
2. Dark green, glossy foliage and a dense, mounded habit.
3. Heat tolerant (USDA hardiness zone 9) in open field tests (Louisiana).
4. Cold hardy (USDA hardiness zone 5) in open field tests (Ohio).
5. Resistant to *Phytophthora* root rot.

COMPARISON TO PARENT VARIETY

'HOLDEN52' is similar in most horticultural characteristics to the seed parent, however, plants of the new cultivar 'HOLDEN52' however differ in the following:

1. The new variety has pink patterned flowers, the seed parent has white flowers.
2. The new variety is more cold hardy than the seed parent.
3. Inflorescence (truss) of the new variety has a pyramidal configuration, compared to the open, floppy inflorescence of the seed parent variety.

'HOLDEN52' is similar in most horticultural characteristics to the pollen parent, however plants of the new cultivar 'HOLDEN52' however differ in the following:

1. 'HOLDEN52' produces pink flowers, the pollen parent produces burgundy red flowers.
2. The new variety tolerates more heat than the pollen parent.
3. The new variety is *Phytophthora* root rot resistant, the pollen parent is not.

COMMERCIAL COMPARISON

'HOLDEN52' can be compared to the commercial variety *Rhododendron hybrida* 'Dandyman Pink', unpatented. Plants of the new cultivar 'HOLDEN52' are similar to plants of 'Dandyman Pink' in most horticultural characteristics, however, plants of the new cultivar 'HOLDEN52' differ in the following:

1. Flowers of 'Holden52' have a stronger, more definite and contrasting color pattern than 'Dandyman Pink'.
2. Foliage of 'Holden52' is darker green and lacks the leaf twisting seen in 'Dandyman Pink'.

'HOLDEN52' can be compared to the commercial variety *Rhododendron hybrida* 'Peppermint Twist', unpatented. Plants of the new cultivar 'HOLDEN52' are similar to plants of 'Peppermint Twist' in most horticultural characteristics, however, plants of the new cultivar 'HOLDEN52' differ in the following:

1. Flowers of 'Holden52' have a stronger, more definite and contrasting color pattern than 'Peppermint Twist', as well as a deeper pink color.
2. Foliage of 'Holden52' is darker green and more glossy.
3. Plant habit of the new variety is more mounded and dense compared to the open, upright habit of 'Peppermint Twist'.
4. The new variety is observed to be somewhat more cold hardy than 'Peppermint Twist'.

BRIEF DESCRIPTION OF THE PHOTOGRAPHS

The accompanying photograph in FIG. 1 illustrates in full color a typical plant of 'Holden52' in the ground at approximately 3 years of age.

Figure 2:
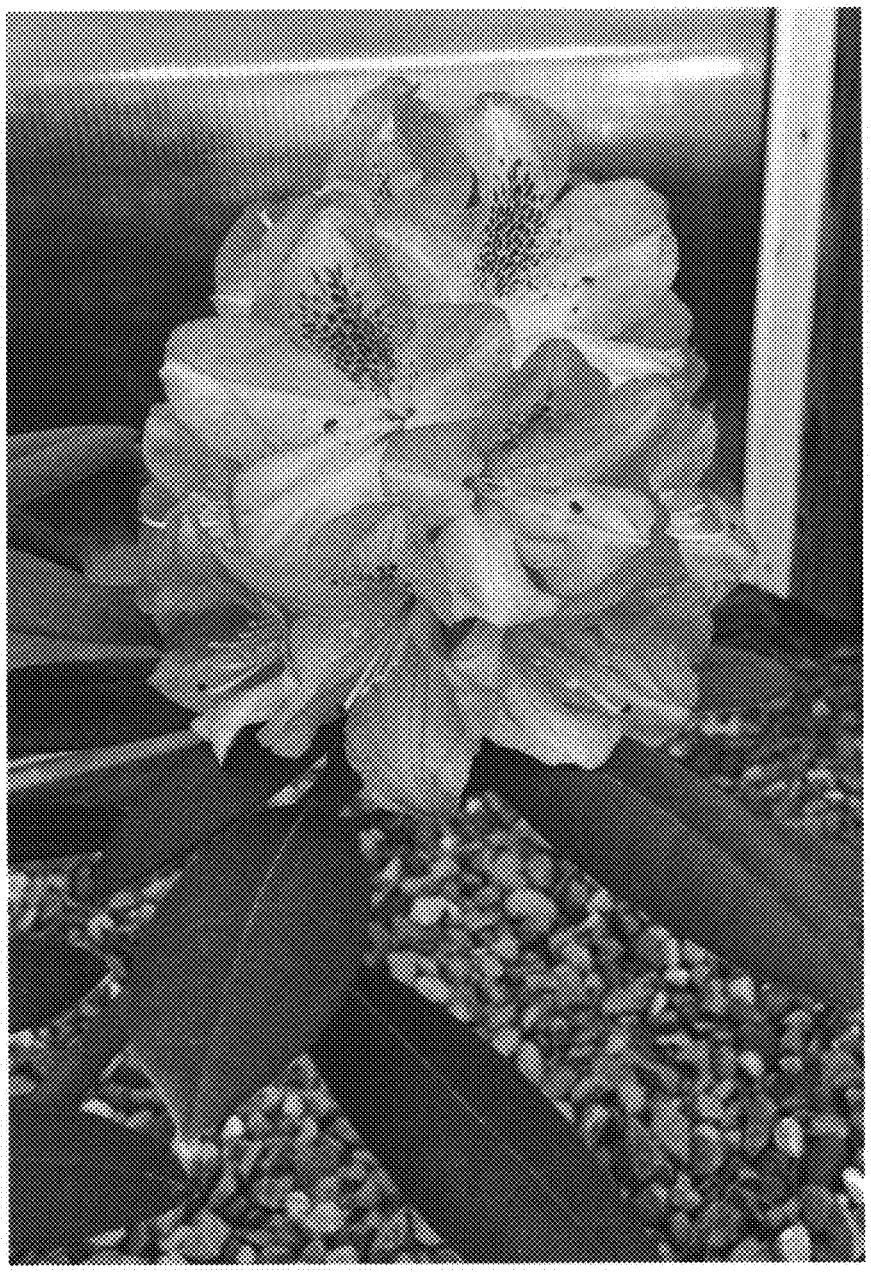

FIG. 2 illustrates a close up of a typical inflorescence of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'HOLDEN52' plants grown outdoors in Loxley, Ala. Plants are approximately 2 years old, in a 3 gallon nursery container. Measurements and numerical values represent averages of typical plant types.

Botanical classification: *Rhododendron hybrida* 'HOLDEN52'.

PROPAGATION

Typically by semi-hardwood cuttings in Spring and Summer.

Root description: Fine, fibrous young roots, well branched. Colored near RHS Brown 200D.

PLANT

Growth habit: Mounded globular evergreen shrub.

Height: Approximately 45 cm to top of foliar and flowering plane.

Growth rate: Rapid.

Plant spread: Approximately 55 cm.

Branching characteristics: About 2 to 4 primary branches from the center of the plant. Branches occur at approximately 35° to 75° angles. Each primary branch has 2 to 4 lateral branches.

Primary branches:

Length of primary branches: Average 20 cm.

Diameter of primary branches: Approximately 0.8 cm.

Primary branch strength: Very strong and difficult to break.

Primary branch color: Young primary branches near RHS Yellow-Green 144C; oldest branches become woody, colored near Brown 200B.

Primary branch texture: Older growth scaly, hirsute.

Lateral branches:

Number of lateral branches: Approximately 2 to 4 per primary branch.

Length of lateral branches: Average 12 cm.

Diameter of lateral branches: Average 0.7 cm.

Lateral branch strength: Very strong, flexible.

Lateral branch color: Immature branches near RHS Greyed-Red 180A, turning, Yellow-Green 144C.

Lateral branch texture: Hirsute.

Internode length: Average 2.0 to 2.5 cm.

Age of plant described: Approximately 2 years.

FOLIAGE

Leaf:

*Type*.—Simple.

*Arrangement*.—Alternate.

*Average length*.—Average range 6.5 to 10.8 cm.

*Average width*.—Average range 3.1 to 3.7 cm.

*Shape of blade*.—Obovate.

*Apex*.—Shallow mucronate.

*Base*.—Broad attenuate.

*Attachment*.—Stalked.

*Margin*.—Entire.

*Texture of top surface*.—Glabrous.

*Texture of bottom surface*.—Glabrous.

*Appearance top surface*.—Mature foliage glossy. Young foliage matte.

*Appearance bottom surface*.—Matte.

*Aspect*.—Concave to somewhat concave.

*Color*.—Young foliage upper side: Near RHS Green 143B. Young foliage under side: Near RHS Green 143C. Mature foliage upper side: Near RHS Green 139A. Mature foliage under side: Near RHS Green 137D.

*Venation*.—Type: Pinnate. Venation color upper side: Near RHS Yellow-Green N144B. Venation color under side: Near RHS Yellow-Green N144D.

*Petiole*.—Length: About 1.0 cm. Diameter: About 0.3 cm. Color: Upper Surface: Near RHS Yellow-Green N144A. Lower Surface: Near RHS Yellow-Green N144B.

FLOWER

Bloom period: Spring.

Flower:

*Arrangement*.—Axillary clusters of single, perfect, open funnel shaped individual flowers. Typically 10 to 15 flowers per cluster.

Inflorescence:

*Height*.—Average 14.0 cm.

*Diameter*.—Average 10.0 cm.

Peduncle:

*Length*.—Average range 3 to 6 cm.

*Diameter*.—0.8 cm.

*Color*.—Near RHS Yellow-Green 144C.

*Texture*.—Glabrous.

*Aspect*.—Straight. Angle of attachment, approximately 15° angle from stem.

Flowers:

*Length*.—Average 6.8 cm.

*Diameter*.—Average 5.7 cm.

*Facing direction*.—Outwardly facing.

*Persistent or self-cleaning*.—Petals self-cleaning.

*Fragrance*.—Very faint.

Tube:

*Tube length*.—Approximately 2.3 cm.

*Tube width a widest point*.—Approximately 1.9 cm.

*Tube width and narrowest point*.—Approximately 0.6 cm.

Petals:

*Unfused petal segments*.—

*Length*.—Approximately 4.7 cm.

*Width*.—Approximately 2.9 cm.

*Apex*.—Rounded.

*Shape of petal*.—Unfused portion, obovate to broad, rounded deltate.

*Petal margin*.—Entire. Aspect very slightly undulating.

*Petal arrangement*.—Overlapping, bilateral symmetry dissecting bottom petal. Petals fused approximately ⅓ fused from base.

*Petal number*.—5.

*Petal texture*.—Smooth.

Color:

*Upper surface at first opening*.—Near RHS Red 54B flushed 53D, 55D at base. Uppermost central petal has linear speckles colored near Red 53D.

*Under surface at first opening*.—Near RHS Red 52B.

*Inner surface at maturity*.—Near RHS Red 54B flushed 53D, Red-Purple 62D. Central streak near White N155B. Uppermost central petal has linear speckles colored near Red 53D.

*Outer surface at maturity*.—Near RHS Red 54B, lower section Red 56A, center streak near Red-Purple 62D.

*Upper surface at fading*.—Main surface near Red-Purple 62D, apex and margin near 55C. Uppermost central petal has linear speckles colored near Red 53D.

*Under surface at fading*.—Main surface near Red 55D, flushed Red-Purple 62C and 62B.

Bud:

*Shape*.—Elliptic.

*Length*.—4.1 cm.

*Diameter*.—2.4 cm.

*Color*.—Near RHS Red 54B, flushed 53D.

Calyx/sepals:

*Quantity per flower*.—5 sepals.

*Shape*.—Narrow deltate.

*Length*.—1.4 cm.

*Width*.—0.8 cm.

*Apex*.—Acute.

*Base*.—Fused.

*Margin*.—Entire.

*Texture*.—Highly pubescent.

*Color*.—Inner Surface: Near RHS Yellow-Green 145A. Outer Surface: Near RHS Yellow-Green 145A.

REPRODUCTIVE ORGANS

Stamens:

*Number*.—5.

*Length*.—3.4 cm.

*Width*.—0.1 cm.

*Color*.—Near RHS Red 56D.

*Anthers*.—Length: Approximately 0.3 cm. Color: Near RHS Yellow-Green 154D. Pollen: Not observed.

Pistil:

*Number*.—1.

*Length*.—5.3 cm.

*Style*.—Length: Average 4.4 cm. Color: Near RHS Red 56D.

*Stigma*.—Globular, colored near 53A.

*Ovary*.—Sericeous texture. Approximately 0.4 cm in diameter. Colored near Yellow-Green 145A.

OTHER CHARACTERISTICS

Disease and pest resistance: Resistance to *Phytophthora* root rot has been observed. Not observed to be susceptible nor resistant to other normal diseases and pests of *Rhododendron*.

Temperature tolerance: USDA Zone 6 though Zone 9.

Fruit/seed production: Not observed to date.

What is claimed is:

1. A new and distinct cultivar of *Rhododendron* plant named 'HOLDEN52' as herein illustrated and described.

* * * * *